United States Patent
Li et al.

(10) Patent No.: US 7,603,899 B2
(45) Date of Patent: Oct. 20, 2009

(54) APPARATUS AND METHOD FOR DETECTING LIQUID LEVEL WITH A PROBE

(75) Inventors: Wei Li, Nanshan (CN); Qilin Liu, Nanshan (CN); Xingcal Zhu, Nanshan (CN)

(73) Assignee: Shenzhen Mindray Bio-Medical Electronics Co., Ltd. (CN)

(*) Notice: Subject to any disclaimer, the term of this patent is extended or adjusted under 35 U.S.C. 154(b) by 59 days.

(21) Appl. No.: 11/634,345

(22) Filed: Dec. 4, 2006

(65) Prior Publication Data

US 2008/0053216 A1    Mar. 6, 2008

(30) Foreign Application Priority Data

Aug. 31, 2006    (CN) .......................... 2006 1 0062402

(51) Int. Cl.
G01F 23/26    (2006.01)
(52) U.S. Cl. .................................. 73/304 C; 73/304 R
(58) Field of Classification Search ............... 73/290 R, 73/304 C
See application file for complete search history.

(56) References Cited

U.S. PATENT DOCUMENTS

| | | | |
|---|---|---|---|
| 5,049,826 A * | 9/1991 | Sasao .......................... | 324/662 |
| 5,415,051 A | 5/1995 | Rokugawa et al. | |
| 5,866,426 A | 2/1999 | Ball | |
| 6,107,810 A | 8/2000 | Ishizawa et al. | |
| 6,148,666 A * | 11/2000 | Roesicke .................. | 73/290 R |
| 7,191,647 B2 * | 3/2007 | Harazin et al. ............ | 73/290 R |

FOREIGN PATENT DOCUMENTS

| | | |
|---|---|---|
| CN | 02250812.0 | 11/2003 |
| CN | 2588334 | 11/2003 |
| JP | 2001004642 | 1/2001 |
| JP | 2001108505 | 4/2001 |
| JP | 2001108506 | 4/2001 |
| JP | 2003057096 | 2/2003 |
| JP | 2003090754 | 3/2003 |
| JP | 2004297982 | 10/2004 |

OTHER PUBLICATIONS

SIPO Search Report for corresponding Chinese application, 2 pages, dated Sep. 20, 2006.
English translation of abstract for Japanese Patent Application No. 2003090754 (reference above).

(Continued)

*Primary Examiner*—Hezron Williams
*Assistant Examiner*—Mark Shabman
(74) *Attorney, Agent, or Firm*—Vista IP Law Group, LLP.

(57) ABSTRACT

The present application discloses a method and apparatus for detecting liquid level with probe, and the method comprising steps of: (A) acquiring a capacitance value of the probe; (B) generating an analog signal corresponding to the acquired capacitance value; (C) converting the generated analog signal into discrete signals at a predetermined sampling interval; (D) increasing or decreasing a counting value according to an amplitude of each the discrete signals, and outputting a liquid level contacting indication signal when the counting value reaches a predetermined counting threshold; and (E) controlling a movement of the probe according to the output liquid level contacting indication signal.

19 Claims, 5 Drawing Sheets

OTHER PUBLICATIONS

English translation of abstract for Japanese Patent Publication No. 2003057096 (reference above).
English translation of abstract for Japanese Patent Publication No. 2001108505 (reference above).
English translation of abstract for Japanese Patent Publication No. 2001004642 (reference above).
English translation of abstract for Chinese Patent No. 2588334 (reference above).

* cited by examiner

APPARATUS AND METHOD FOR DETECTING LIQUID LEVEL WITH A PROBE

RELATED APPLICATION DATA

This application claims priority to Chinese Application No. 200610062402.X, filed on Aug. 31, 2006, the entire disclosure of which is expressly incorporated by reference herein.

TECHNICAL FIELD

The present application relates to a liquid level sensing apparatus, and more particularly, relates to an apparatus and method for detecting liquid level of a liquid sample or a reagent by automatic biochemical analyzer during sampling process.

BACKGROUND

When the biochemical analyzer analyzes body fluid, it first takes liquid samples. Driven by a motor, a pipetting probe is moved downward in a tube, and when the probe is in contact with the liquid surface, the motor must be stopped to prevent that the probe encounters the bottom of the tube and non-necessary body fluid is sucked. After sucked body fluid, driven by the motor, the probe is moved upward to return. Therefore, liquid level detecting must be carried out for biochemical analysis. When the probe is in contact with the liquid surface, a liquid surface contacting indication signal needs to be output to a control unit for controlling the motor, so as to control the motor to stop. The prior liquid level detecting technologies for the automatic biochemical analyzer mainly include a capacitance change type liquid level detecting, a pressure sensing type liquid level detecting, a wireless transmission and receiving type liquid level detecting and so on.

The capacitance change type liquid level detecting technology detects liquid level based on a change in capacitance of the pipetting probe, and is widely applied because of its characteristics such as high sensitivity, not affecting the accuracy of the sucked liquid samples and so on. In U.S. Pat. No. 6,107,810, a method for capacitance change type liquid level detecting is described, wherein, the pipetting probe is a single tube probe and is connected to a detecting circuit, the sample disk or reagent disk is grounded, and liquid level is detected by detecting a change in capacitance between the probe and the ground. The single tube probe for the method is susceptible to outside interference, and thus there is high requirement for the grounding of the sample disk.

A China patent, named "liquid level detector for biochemical analysis" (Patent No. CN02250812.0, publication date Nov. 26, 2003), disclosed an apparatus for detecting liquid level with capacitance change, wherein, the pipetting probe adopts a double-layer coaxial probe structure, the inner and outer probe tubes are made by a medically used stainless steel and equivalent to two electrodes of a capacitance, and an insulated casing is inserted between them. When the tip of the probe is in contact with the liquid level, the dielectric constant between the two electrodes varies and thus the capacitance of the probe is changed, consequently, the liquid level is detected by sensing the change in capacitance.

This apparatus generally comprises: a probe, an oscillation and frequency division circuit, a phase locked loop (PLL), an amplifier circuit, a comparison circuit and a control unit. The change in capacitance of the probe results in the change of oscillation frequency of the PLL and the change of oscillation frequency is converted into an electrical level signal. The electrical level signal is amplified by the amplifier circuit and the amplified signal is compared by the comparison circuit. Then, the comparison circuit outputs a signal to the control unit to control the motor to stop rotation. The pipetting probe then stops moving and goes back after sucking samples, and thus the object of the liquid level detecting is achieved.

However, this scheme for detecting liquid level is implemented by purely analog circuits, and a liquid level contacting indication signal will be output once the voltage value indicated by a current voltage signal is greater than a predetermined threshold. Therefore, this scheme has poor anti-interference performance, is susceptible to interference and causes false detection, and thus resulting in the control error for the motor. In order to improve the reliability of detection, namely the anti-interference performance, the only way to implement is by increasing the comparison threshold of the comparison circuit. However, simply increasing the comparison threshold results in the dropping of the sensitivity for one aspect, and needs a larger amount of reagents and samples for another aspect. With the development of the automatic biochemical analyzer technology and the environment protection requirements, laboratories are using less and less amount of reagents and samples, which set higher demands on detection sensitivity. However, the prior scheme for detecting liquid level is especially not suitable for detecting liquid level of a small amount of liquid.

SUMMARY

An object is to provide an apparatus and method for detecting liquid level with a probe so as to solve the above problem, which is suitable for not only a large amount of reagents and samples but also a small amount of reagents and samples, and can improve not only the anti-interference performance of the apparatus but also the detection sensitivity.

Another object is to provide an apparatus and method for detecting liquid level with a probe, which can select a suitable liquid level detecting method according to the amount of reagents and samples, and thus the anti-interference performance of the apparatus can be further improved.

To achieve the above objects, the present application provides an apparatus for detecting liquid level with a probe, comprising: a pipetting probe for sucking liquid to be detected and outputting a capacitance value itself; a generation module for receiving the capacitance value output from the pipetting probe and generating an analog signal corresponding to the received capacitance value; a signal converting module for converting the generated analog signal into discrete signals at a predetermined sampling interval; a signal processing module for increasing or decreasing a counting value according to a magnitude of each of the discrete signals, and outputting a liquid level contacting indication signal when the counting value reaches a predetermined counting threshold; and a control module for controlling a movement of the pipetting probe according to the output liquid level contacting indication signal.

The signal processing module further comprises: a first judging unit (100, 102, 104) for judging if a current discrete signal in the discrete signals satisfies a condition that its value is greater than a first threshold value (V1) and a slope between it and a previous discrete signal is greater than a predetermined slope threshold; a first counting unit (106) for increasing a first counting value if it is judged that the current discrete signal satisfies the condition, otherwise decreasing the first counting value; and a first output unit (108) for outputting the liquid level contacting indication signal when the first counting value reaches a first counting threshold.

The signal processing module further comprises: a second judging unit for judging if the current discrete signal is greater than a second threshold value (Vh) that is greater than the first threshold value; a second counting unit (110) for increasing a second counting value if the current discrete signal is greater than the second threshold value, otherwise decreasing the second counting value; and a second output unit (112) for outputting the liquid level contacting indication signal when the second counting value reached a second counting threshold.

To achieve the above objects, the present application further provides a method for detecting liquid level with a probe, comprising steps of: (A) acquiring a capacitance value of the probe; (B) generating an analog signal corresponding to the acquired capacitance value; (C) converting the generated analog signal into discrete signals at a predetermined sampling interval; (D) increasing or decreasing a counting value according to a magnitude of each of the discrete signals, and outputting a liquid level contacting indication signal when the counting value reaches a predetermined counting threshold; and (E) controlling a movement of the probe according to the output liquid level contacting indication signal.

The step (D) further comprises: judging if a current discrete signal in the discrete signals satisfies a condition that its value is greater than a first threshold value (Vl) and a slope between it and a previous discrete signal is greater than a predetermined slope threshold; increasing a first counting value if it is judged that the current discrete signal satisfies the condition, otherwise decreasing the first counting value; and outputting the liquid level contacting indication signal when the first counting value reaches a first counting threshold.

The step (D) further comprises: judging if the current discrete signal is greater than a second threshold value (Vh) that is greater than the first threshold value; increasing a second counting value if the current discrete signal is greater than the second threshold value, otherwise decreasing the second counting value; and outputting the liquid level contacting indication signal when the second counting value reaches a second counting threshold.

The advantageous effects are: 1) in the embodiments described herein, a counting value is increased or decreased based on whether the signal and its slope are greater than a first predetermined threshold and a slope threshold respectively or whether the signal is greater than a second predetermined threshold, and a liquid level contacting indication signal is outputted to the control unit when the counting value reaches a predetermining counting threshold. Therefore, the first predetermined threshold may be set to a lower value such as a value when the probe just reaches liquid level and thus the embodiments can improve the detection sensitivity. Moreover, a liquid level contacting indication signal is outputted to the control unit only when the counting value reaches the predetermining counting threshold, instead when the signal is greater than the predetermined threshold, so the present embodiments can improve the anti-interference performance; 2) the embodiments selects, based on the amount of liquid to be detected, a suitable detecting method from the slope detecting method and the amplitude detecting method to detect liquid level, therefore, the embodiments can improve the detection sensitivity and the anti-interference performance.

These and other objects, advantages and features of the embodiments will become apparent from the following description thereof taken in conjunction with the accompanying drawings.

DETAILED DESCRIPTION

Figure 1:
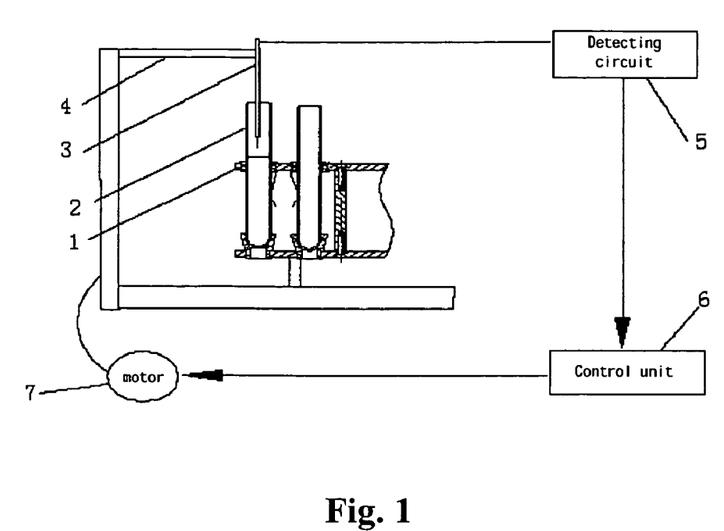
FIG. 1 is a diagram showing an apparatus for detecting liquid level according to an embodiment.

FIG. 1 is a diagram showing an apparatus for detecting liquid level according to an embodiment. As shown in FIG. 1, the apparatus for detecting liquid level comprises a pipetting probe 3, a detecting circuit 5, a container 2 for containing liquid, a disk 1 for fixing the container 2 and a pipetting probe moving control means. Wherein, the pipetting probe moving control means comprises a motor 7, a probe arm 4, a control unit 6, and so on. Wherein, the probe arm 4 is used to fix the pipetting probe 3 that may be a double-layer pipetting probe or a single tube probe. The control unit 6 controls the motor 7 such that the pipetting probe 3 may perform the actions such as startup, vertical movement, stop, and so on. When the tip of the pipetting probe 3 is in contact with the liquid level in the container 2, the capacitance value of the probe is increased suddenly. The detecting circuit 5 converts the capacitance change information into an electrical signal and output it to the control unit 6. The control unit 6 immediately sends the motor 7 a command to stop the movement of the pipetting probe 3 and then start other actions, such as sucking the liquid and going back.

Figure 2:
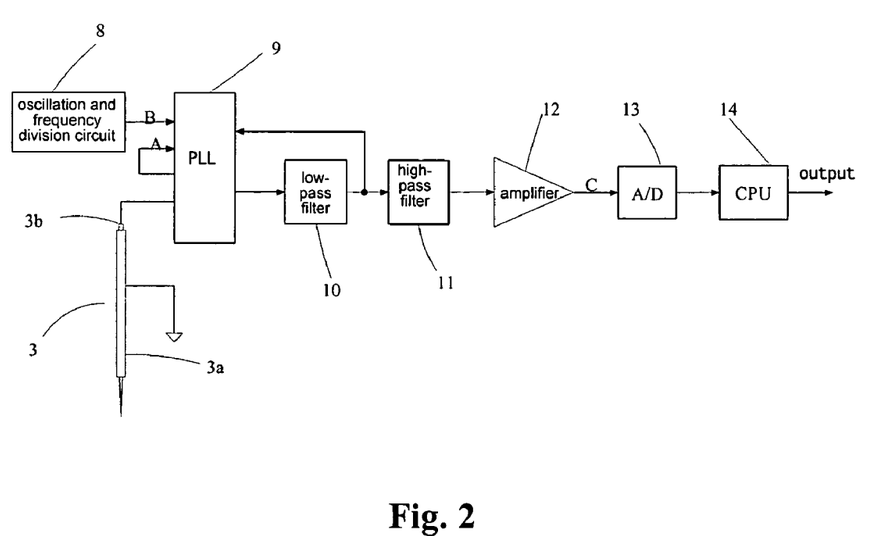
FIG. 2 is a diagram showing the detecting circuit according to an embodiment.

FIG. 2 is a diagram showing the detecting circuit according to an embodiment. As shown in FIG. 2, the detecting circuit 5 comprises a generation module, a low-pass filter circuit 10, a high-pass filter circuit 11, an amplifier 12, an A/D converter 13 and a signal processing module 14. The generation module receives the capacitance value output from the pipetting probe 3 and generates an analog voltage signal corresponding to the capacitance value. The generation module comprises an oscillation and frequency division circuit 8 and a PLL integrated circuit 9. In FIG. 2, the pipetting probe 3 is a double-layer probe, wherein a wire coupled to a conductive outer probe tube 3a is grounded and connected with the ground of the detecting circuit, and a wire coupled to a conductive inner probe tube 3b is connected with a pin in the PLL integrated circuit 9, via which a voltage controlled oscillator in the PLL integrated circuit 9 should be connected with an oscillation capacitance. The voltage controlled oscillator outputs an oscillation signal A to a phase detector in the PLL integrated circuit 9 and a reference signal B from the oscillation and frequency division circuit 8 is also inputted to the phase detector in the PLL integrated circuit 9. When the pipetting probe 3 is not in contact with the liquid level, the two oscillation signals A and B have the same frequency and the PLL integrated circuit 9 outputs a lower electrical level; when the pipetting probe 3 is moved downward and is in contact with the liquid level, its capacitance value is increased suddenly, and the frequency of the signal A output from the voltage controlled oscillator is changed correspondingly. Because the frequencies of the two oscillation signals A and B are different now, the electrical level output by the PLL integrated circuit 9 is increased. The increased electrical level is filtered by the low-pass filter circuit 10 and the high-pass filter circuit 11, amplified by the amplifier 12, inputted to the A/D converter 13 for performing analog-to-digital conversion and executed a software determination by the signal processing module 14 for outputting a liquid level contacting indication signal to the control unit 6. Then, the control unit 6 controls the motor 7 to stop rotation, and the pipetting probe 3 stops moving and will goes back after sucking samples.

Figure 3:
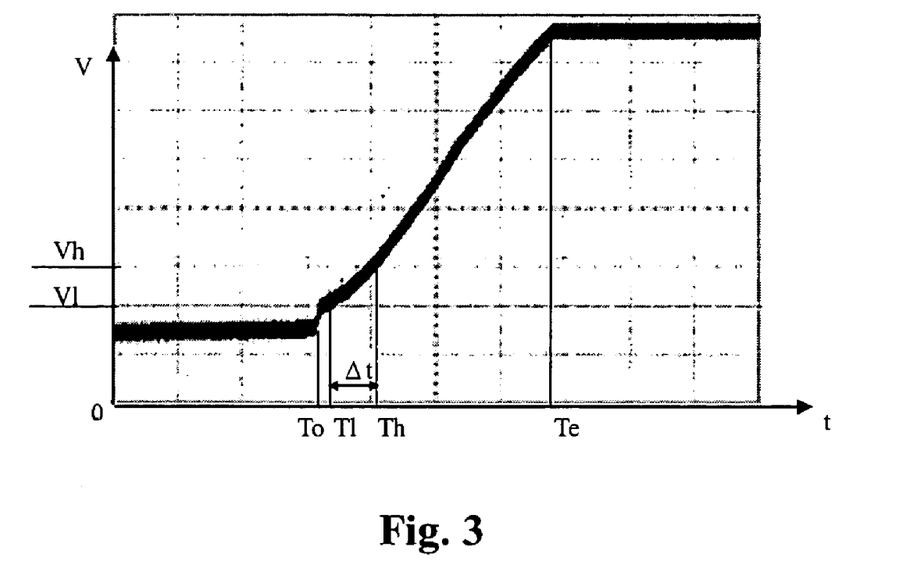
FIG. 3 is an amplitude-time waveform diagram showing a simulated liquid level detecting signal when a large amount of liquid is detected.
Figure 4:
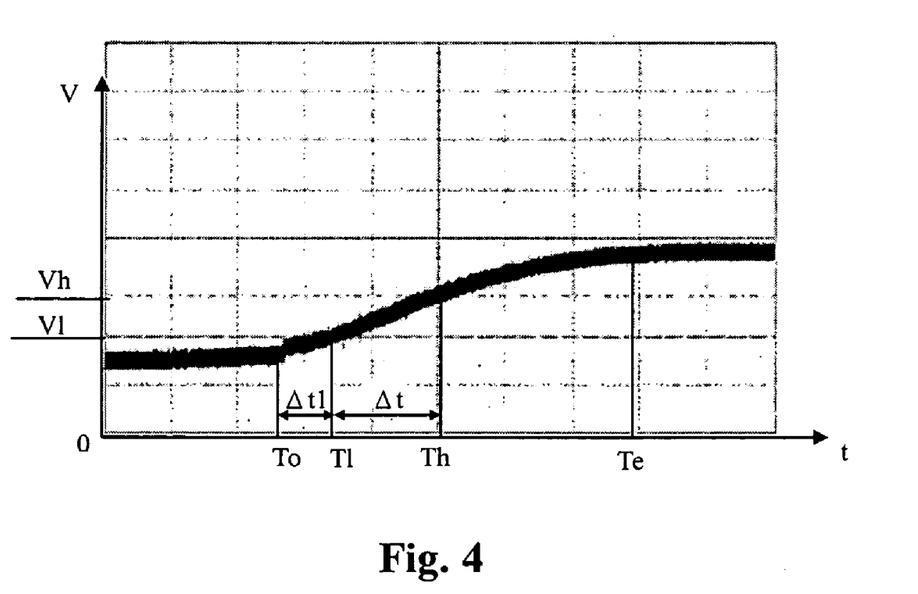
FIG. 4 is an amplitude-time waveform diagram showing a simulated liquid level detecting signal when a small amount of liquid is detected.

FIG. 3 and FIG. 4 shows a simulated liquid level detecting signal (namely, the signal C output from the amplifier 12) during the process that the pipetting probe 3 moves vertically from top to bottom until in contact with the liquid level. It is apparently that the simulated liquid level detecting signal increases in amplitude gradually. Assuming that Vl is a low amplitude threshold, Vh is a high amplitude threshold and To denotes the time when the probe is in contact with the liquid level. As show in FIGS. 3 and 4, the simulated liquid level detecting signal changes suddenly at the time To and then increases gradually. When a period of time elapses, the amplitude of the signal is Vl at time T1, and after a time delay $\Delta t$, the amplitude of the signal increases to Vh. Finally, the amplitude of the signal is saturated at time Te. When a large amount of liquid is detected, as shown in FIG. 3, the amplitude of the signal increases faster and increases to the high amplitude threshold Vh in a very short time. When a small amount of liquid such as 80 uL, 100 uL or the like is detected, because the sensitivity of the capacitance of the probe is drop with respect to the small amount of liquid, the change in capacitance of the probe will decrease largely. Accordingly, when the probe is in contact with the liquid level, the amplitude of the simulated liquid level detecting signal is smaller, and the slope of the signal is smaller too, that is, as shown in FIG. 4, the time delay $\Delta t1$ for the amplitude of the simulated liquid level detecting signal to increase from the initial value to Vl and the time delay $\Delta t$ for the amplitude thereof to increase from Vl to Vh are larger. Further, although the signal in FIG. 4 reaches its maximum amplitude at time Te, the maximum amplitude is much smaller than that in FIG. 3.

Based on the characteristics of the liquid level detecting signal as disclosed in FIG. 3 and FIG. 4, an embodiment adopts a slope detecting method when the small amount of liquid is detected and a amplitude detecting method when the large amount of liquid is detected. Specifically, the low amplitude threshold Vl, the high amplitude threshold Vh and a slope threshold Sp is preset, and when the amplitude of the liquid level detecting signal is greater than the low threshold Vl and less than the high threshold Vh, the slope detecting method is carried out; when the amplitude of the liquid level detecting signal is greater than the high threshold Vh, the slope detecting method is stopped and the amplitude detecting method is carried out.

Figure 5:
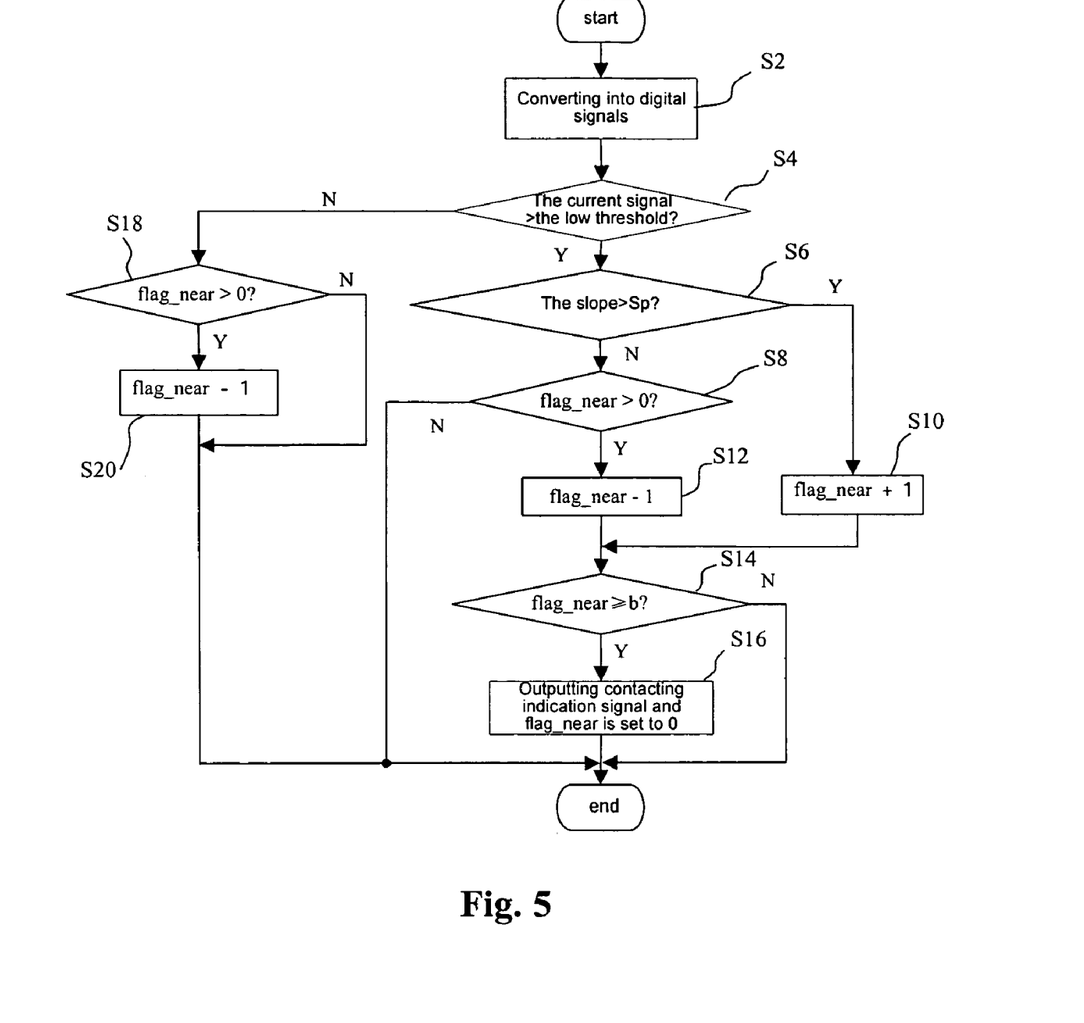
FIG. 5 is a flow chat showing the slope detecting method according to an embodiment.

The flow chart of the slope detecting method is shown in FIG. 5. The slope detecting method is explained in detail below in conjunction with FIG. 5.

At step S2, the analog signal C output from the amplifier 12 is sampled and then converted into digital signals, wherein the sampling interval is $\Delta T$.

At step S4, a currently converted digital signal is taken as a current digital signal, and whether or not the amplitude of the current digital signal is greater than a predetermined low threshold Vl is determined. If the determination is YES, the flow proceeds to step S6, otherwise the flow proceeds to step S18.

At step S6, a slope of two adjacent digital signals is calculated, that is, the ratio of the difference between the current digital signal and the previous digital signal to the sampling interval $\Delta T$, and whether or not the slope is greater than the slope threshold Sp is determined. If the determination is YES, the flow proceeds to step S10, otherwise the flow proceeds to step S8.

At step S10, the value of a first liquid level flag counter flag_near is increased by 1 (the value of the counter flag near will be set to zero every time when startup or the liquid level contacting indication signal is output.), and then the flow proceeds to step S14.

At step S8, whether or not the value of the counter flag_near is greater than 0 is determined. If the determination is YES, the flow proceeds to step S12, otherwise the processing of the current digital signal is finished and a next digital signal is taken as the current digital signal to restart the flow.

At step S12, the value of the counter flag_near is decreased by 1 to eliminate a sudden change of the signal. If the previous digital signal is in accord with the slope determination condition and the current digital signal is not in accord with the slope determination condition, this means that the previous digital signal may be an interference signal. Therefore, the value of the counter flag_near is decreased by 1 such that the interference signal will not interfere latter determinations.

At step S14, whether or not the value of the first counter flag_near is greater than or equal to a first predetermined value b is determined. The first predetermined value b is set by experience. The value b can't be too small (e.g., less than 3), because the small value b easily results in false determination. Moreover, the value b can't be too big (e.g., greater than 10), because if it is too big, the pipetting probe will be inserted too deep under the liquid level, which will easily cause crosscontamination, and even when the pipetting probe moves downward to the vertical limit position, the liquid level contacting indication signal is still not output, this will result in a false reporting of no liquid. Therefore, the first predetermined value b generally may be set to 5. If the value of the first counter flag_near is greater than or equal to the first predetermined value b, this means the pipetting probe is in contact with liquid level, and then the flow proceeds to step S16, otherwise the processing of the current digital signal is finished and a next digital signal is taken as the current digital signal to continue the flow.

At step S16, the liquid level contacting indication signal is output to the control unit, and the control unit controls the motor to stop, so as to stop the pipetting probe moving downward; meanwhile, the value of the first counter flag_near is set to zero. After step S16 is finished, the flow is ended until starting the next liquid level detecting.

At step S18, whether or not the value of the first counter flag_near is greater than 0 is determined. If the determination is YES, the flow proceeds to step S20, otherwise the flow is ended until starting the next liquid level detecting.

At step S20, the value of the first counter flag_near is decreased by 1.

The slope detecting method is suitable for detecting liquid level of the small amount of liquid, because the liquid level detecting signal needs a long time to increase to the high threshold Vh but only needs a short time to increase to the low threshold Vl, and although the amplitude of the liquid level detecting signal is small at the time when the signal reaches the low amplitude threshold Vl, the liquid level detecting signal still will increasing gradually. Consequently, it is suitable for carrying out the detecting by using the slope detecting method. In the slope detecting method, the signal is sampled at time interval ΔT and the sampled signals are converted into digital signals; the slopes of every adjacent two of the b+1 digital signals are calculated, and for each of the slopes, if it is greater than the slope threshold Sp, the first counter is creased by 1, otherwise the counter is decreased by 1; when the value of the counter reaches the predetermined threshold, this means that the probe is in contact with the liquid level and a liquid level contacting indication signal is output to the control unit. Under normal conditions, after the amplitude of the simulated liquid level detecting signal is greater than the low threshold Vl, it only needs a time period of five times ΔT (when b=5) to output the indication signal to the control unit 6. The low threshold Vl may have a lower value, and thus the detection sensitivity may be improved; moreover, only when a plurality of slopes are greater than the slope threshold, the liquid level contacting indication signal is then output, this results in the improving of the anti-interference performance of the detecting, namely, the improving of the reliability of the detecting.

When the sampling interval ΔT is adjusted to an appropriate value, the detection sensitivity may be improved effectively. The sampling interval ΔT is an experiential value and relates to parameters such as the speed of the motor, the sampling rate of the signal processing module, and so on.

Figure 6:
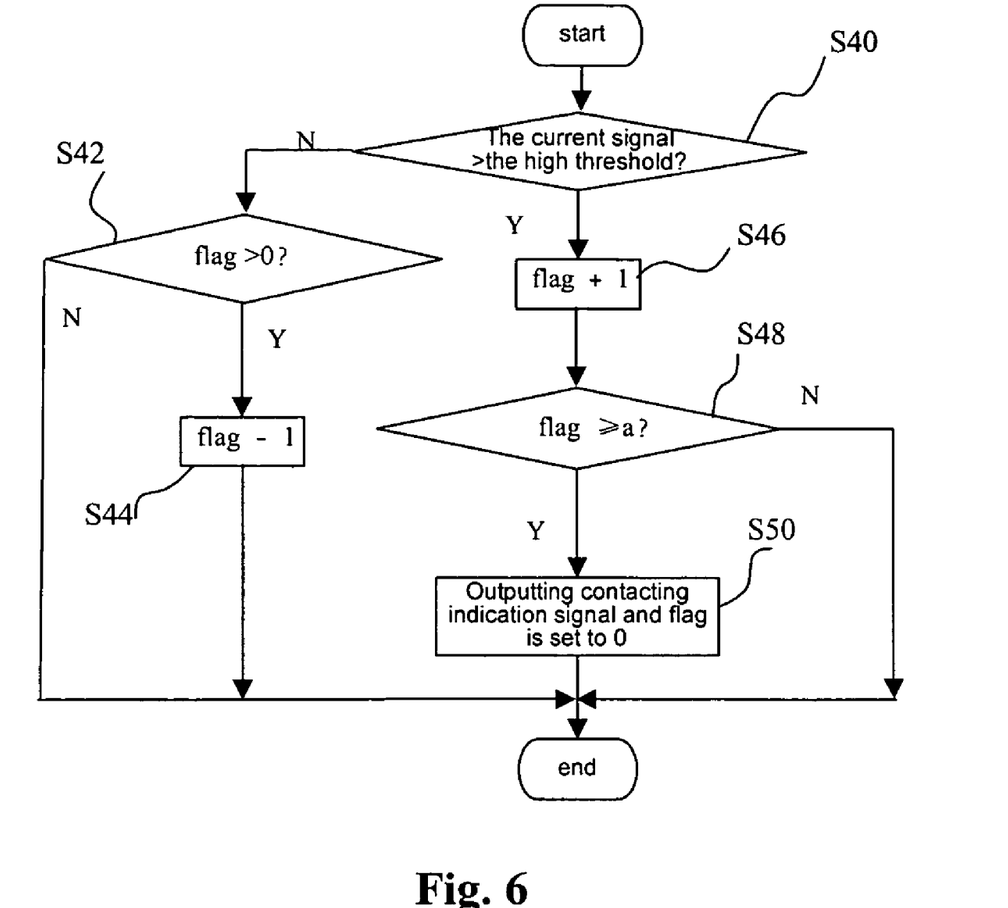
FIG. 6 is a flow chat showing the amplitude detecting method according to an embodiment.

The flow chat of the amplitude detecting method is shown in FIG. 6. The amplitude detecting method is explained in detail below in conjunction with FIG. 6.

At step S40, a currently converted digital signal is taken as a current digital signal, and whether or not the current digital signal is greater than or equal to the high threshold Vh is determined. If the determination is YES, the flow proceeds to step S46, otherwise the flow proceeds to step S42.

At step S42, whether or not the value of a second liquid level flag counter flag is greater than 0 is determined. If the determination is YES, the flow proceeds to step S44, otherwise the processing of the current digital signal is ended and a next digital signal is taken as the current digital signal to restart the flow.

At step S44, the value of the second counter flag is decreased by 1 to eliminate a sudden change of the signal. If a previous digital signal is greater than or equal to the high threshold Vh but the current digital signal is less than the high threshold Vh, this means that the previous digital signal may be an interference signal. Therefore, the value of the second counter flag is decreased by 1 such that the interference signal will not interfere latter determinations.

At step S46, the value of the second counter flag is increased by 1 (the value of the second counter flag will be set to zero every time when startup or the liquid level contacting indication signal is output.), and then the flow proceeds to step S48.

At step S48, whether or not the value of the second counter flag is greater than or equal to a second predetermined value a is determined. The second predetermined value a is set by experience and is generally set as 3. If the value of the second counter flag is greater than or equal to the second predetermined value a, this means the pipetting probe is in contact with liquid level, then the flow proceeds to step S50. If the value of the second counter flag is less than the second predetermined value a, then the processing of the current digital signal is ended and a next digital signal is taken as the current digital signal to restart the flow.

At step S50, the liquid level contacting indication signal is output to the control unit to control the motor to stop, so as to stop the pipetting probe moving downward; meanwhile, the value of the second counter flag is set as zero. Then, the flow is finished until starting the next liquid level detecting.

The amplitude detecting method is suitable for detecting liquid level of a large amount of liquid. After the pipetting probe is in contact with the liquid surface, the amplitude of the signal increases to the high threshold Vh in a short time, so at this time the slope detecting method is stopped and the amplitude detecting method is started. In the amplitude detecting method, the second counter flag and the high threshold Vh are preset; for each of the digital signals, if it is greater than the high threshold Vh, the value of the second counter is increased by 1, otherwise the value of the second counter is decreased by 1; when the value of the second counter reaches a predetermined value, this means that the probe is in contact with liquid level and a liquid level contacting indication signal is output to the control unit. Since the liquid level contacting indication signal is output to the control unit only when the second counter reaches the predetermined value, instead when the signal is greater than the threshold, the amplitude detecting method can improve the anti-interference performance effectively compared with the prior art. Moreover, since the amplitude detecting method has the anti-interference performance, the high threshold Vh may be set as a lower value and thus the detection sensitivity can be improved substantially.

Figure 7:
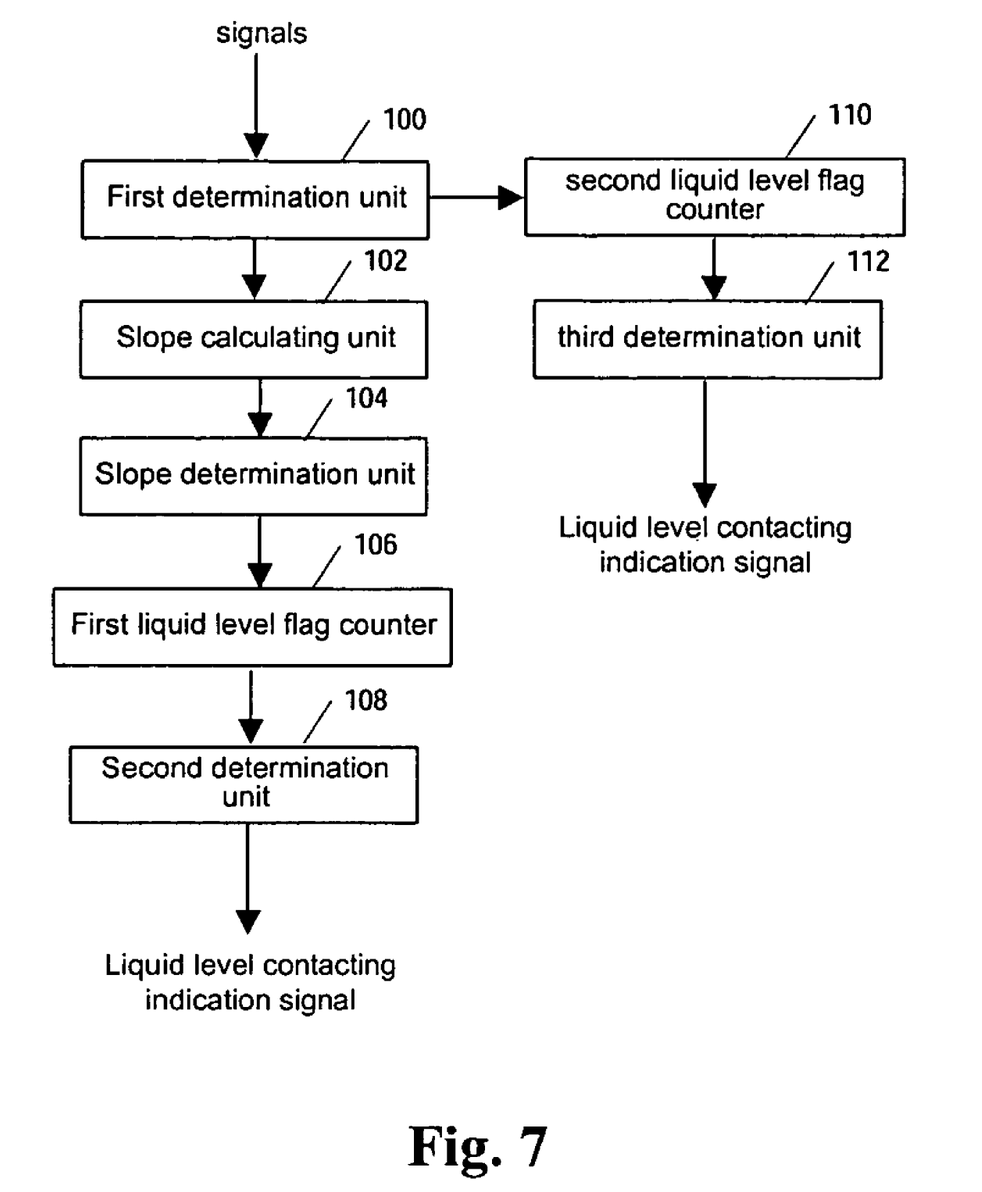
FIG. 7 is a block diagram showing the signal processing module according to an embodiment.

The above slope detecting method and amplitude detecting method are mainly implemented in the signal processing module 14. FIG. 7 shows a diagram of the signal processing module according to an embodiment. As shown in FIG. 7, the signal processing module 14 comprises a first determination unit 100, a slope calculating unit 102, a slope determination unit 104, a first liquid level flag counter 106, a second determination unit 108, a second liquid level flag counter 110 and a third determination unit 112. The first determination unit 100 receives digital signals output from the A/D converter 13 and determines if the current digital signal is greater than the low threshold Vl. When the current digital signal is greater than the low threshold Vl, a first control signal is output to the slope calculating unit 102. After receiving the first control signal, the slope calculating unit 102 calculates a slope between the current digital signal and the previous digital signal. Then the slope determination unit 104 receives the slope output from the slope calculating unit 102 and determines if the slope is greater than the slope threshold Sp. If the determination is YES, a second control signal is output to the first liquid level flag counter 106 and then the first counter increases by 1; if the determination is NO, a third control signal is output to the first liquid level flag counter 106 and then the first counter decreases by 1. The second determination unit 108 continuously determines if the value of the first liquid surface flag counter 106 is greater than or equal to a first predetermined value b, and when the value of the first liquid level flag counter 106 is greater than or equal to the first predetermined value b, the liquid level contacting indication signal is output to the control unit 6.

When the first determination unit 100 determines that the current digital signal is greater than or equal to the high threshold, a fourth control signal is output to the second liquid level flag counter 110, and meanwhile a sixth control signal is outputted to the slope calculating unit 102. After receiving the sixth control signal, the slope calculating unit 102 stops calculating the slope. After receiving the fourth control signal, the second liquid level flag counter 110 increases by 1. Thereafter, when the first determination unit 100 determines that the current digital signal is less than the high threshold, a fifth control signal is output to the second liquid level flag counter 110. After receiving the fifth control signal, the second liquid level flag counter 110 decreases by 1. The third determination unit 112 continuously determines if the value of the second liquid level flag counter 110 is greater than or equal to the second predetermined value a, and when the value of the second liquid surface flag counter 110 is greater than or equal to the first predetermined value a, the liquid level contacting indication signal is output to the control unit 6.

In some cases, the slope detecting method is also suitable for detecting liquid level of a large amount of liquid, and thus another embodiment only employs the slope detecting method and does not use the amplitude detecting method.

Furthermore, although in above embodiment, the slope detecting method is stopped when the amplitude detecting method is executed, the present invention should not be limited to this. Actually, in other embodiments, the amplitude detecting method and the slope detecting method can be executed at the same time.

Furthermore, although in above embodiment, the analog signal is converted into digital signals, the present invention should not be limited to this. In other embodiments, the analog signal may be converted into discrete signals such as sampled signals obtained by directly sampling the analog signal or quantified signals obtained by quantifying the sampled signals, and so on, and the slope detecting method and the amplitude detecting method are carried out based the discrete signals.

It will be obvious to those skilled in the art that various modifications may be made to the apparatus and method for detecting liquid level as disclosed without departing from the spirit of the present invention. Thus, the scope of the present invention is to be defined by the appended claims herein.

What is claimed is:

1. An apparatus for detecting liquid level with a probe, comprising:
   a pipetting probe configured for causing output of a capacitance value;
   a generation module configured for generating an analog signal corresponding to the capacitance value;
   a signal converting module configured for converting the analog signal into discrete signals;
   a signal processing module configured for causing a determination of whether to adopt a slope detecting process or an amplitude detecting process for processing the discrete signals based at least upon an amount of liquid detected and for causing to output a liquid level contacting indication signal; and
   a control module configured for controlling a movement of the pipetting probe based at least upon the liquid level contacting indication signal.

2. The apparatus of claim 1, wherein, the signal processing module further comprises:
   a first judgment unit for judging if a current discrete signal in the discrete signals satisfies a condition that its value is greater than a first threshold value (Vl) and a slope between it and a previous discrete signal is greater than a predetermined slope threshold;
   a first counting unit for increasing a first counting value if it is judged that the current discrete signal satisfies the condition, otherwise decreasing the first counting value; and a first output unit for outputting the liquid level contacting indication signal when the first counting value reaches a first counting threshold.

3. The apparatus of claim 2, further comprising:
   a second judgment unit for judging if the current discrete signal is greater than a second threshold value (Vh) that is greater than the first threshold value;
   a second counting unit for increasing a second counting value if the current discrete signal is greater than the second threshold value, otherwise decreasing the second counting value; and
   a second output unit for outputting the liquid level contacting indication signal when the second counting value reaches a second counting threshold 4. The apparatus of claim 3, further comprising:
   where the current discrete signal is greater than the second threshold value, means for stopping a first determination unit.

5. The apparatus of claim 1, wherein the signal converting module is an AID converter, and the discrete signals are digital signals.

6. The apparatus of claim 1, further comprising:
   a filter unit for filtering the analog signal; and
   an amplifier unit for amplifying the filtered analog signal and outputting it to the signal converting module.

7. The apparatus of claim 1, the generation module further comprising:
   an oscillation and frequency division circuit for generating and outputting a reference signal; and
   a PLL integrated circuit for generating an oscillation signal corresponding to the capacitance value of the pipetting probe, and based on the reference signal generated by the oscillation and frequency division circuit and the oscillation signal, generating the analog signal.

8. The apparatus of claim 1, in which the signal processing module is further configured for causing an increment or a decrement of a counting value based at least upon a result of the slope detecting process or of the amplitude detecting process, and the counting value causes the act of outputting the liquid level contacting indication signal when the counting value exceeds a counting threshold.

9. The apparatus of claim 8, wherein the signal processing module is further configured for causing a second determination of whether one or more of the discrete signals constitute a noise signal based at least upon the result.

10. The apparatus of claim 9, wherein the signal processing module is configured for causing the second determination of the noise signal by examining at least two contiguous signals of the discrete signals.

11. The apparatus of claim 1, wherein the signal processing module is configured for causing the determination further based at least on a time period for the liquid level detecting signal to reach a first time period.

12. A method for detecting liquid level with a probe, comprising steps of:
   identifying a capacitance value of the probe;
   generating an analog signal corresponding to the capacitance value;
   converting the generated analog signal into discrete signals;
   determining whether to adopt a slope detecting process or an amplitude detecting process for processing the discrete signals and outputting a liquid level contacting indication signal; and
   controlling a movement of the probe based at least upon the output liquid level contacting indication signal.

13. The method of claim 12, wherein the act of outputting the liquid level contacting indication further comprises;
   judging if a current discrete signal in the discrete signals satisfies a condition that its value is greater than a first threshold value (Vl) and a slope between it and a previous discrete signal is greater than a predetermined slope threshold;

increasing a first counting value if it is judged that the current discrete signal satisfied the condition, otherwise decreasing the first counting value; and outputting the liquid level contacting indication signal when the first counting value reaches a first counting threshold.

14. The method of claim 13, wherein, further comprising:

judging if the current discrete signal is greater than a second threshold value (Vh) that is greater than the first threshold value;

increasing a second counting value if the current discrete signal is greater than the second threshold value, otherwise decreasing the second counting value; and outputting the liquid level contacting indication signal when the second counting value reaches a second counting threshold.

15. The method of claim 14, wherein, further comprising:

when it is judged that the current discrete signal is greater than the second threshold value, the step of determining if the current discrete signal is greater than a first threshold value (Vl) and a slope between it and a previous discrete signal is greater than a predetermined slope threshold is stopped.

16. The method of claim 12, wherein the discrete signals are digital signals.

17. The method of claim 12, further comprising:

incrementing or decrementing a counting value based at least upon a result of the slope detecting process or the amplitude detecting process, wherein the counting value causes the act of outputting the liquid level contacting indication signal when the counting value exceeds a counting threshold.

18. The method of claim 17, further comprising:

determining whether or not one or more of the discrete signals constitute a noise signal based at least upon the result.

19. The method of claim 18, wherein the act of determining whether or not the one or more of the discrete signals constitute a noise signal by examining at least two contiguous signals of the discrete signals.

* * * * *